US011096555B2

(12) United States Patent
Harrah et al.

(10) Patent No.: US 11,096,555 B2
(45) Date of Patent: Aug. 24, 2021

(54) MEDICAL INSTRUMENT SYSTEM

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Derrick Lenz, Pompton Plains, NJ (US); Arpita Banerjee, Bangalore (IN); Sandesh Gavade, Bangalore (IN); Pavan Misra, Bangalore (IN); Abhijit Takale, Pune (IN)

(73) Assignee: Boston Scientific Scimed, Inc., Maple Grove, MN (US)

(*) Notice: Subject to any disclaimer, the term of this patent is extended or adjusted under 35 U.S.C. 154(b) by 649 days.

(21) Appl. No.: 15/416,841

(22) Filed: Jan. 26, 2017

(65) Prior Publication Data

US 2017/0215695 A1 Aug. 3, 2017

Related U.S. Application Data

(60) Provisional application No. 62/288,868, filed on Jan. 29, 2016.

(51) Int. Cl.

| *A61B 1/00* | (2006.01) |
|---|---|
| *A61B 90/50* | (2016.01) |
| *A61B 34/00* | (2016.01) |
| *A61B 34/30* | (2016.01) |
| *A61B 1/015* | (2006.01) |
| *A61B 1/04* | (2006.01) |
| *A61B 1/06* | (2006.01) |
| *A61B 1/307* | (2006.01) |

(Continued)

(52) U.S. Cl.
CPC ........ *A61B 1/00048* (2013.01); *A61B 1/0016* (2013.01); *A61B 1/00039* (2013.01); *A61B 1/00052* (2013.01); *A61B 1/00133* (2013.01); *A61B 1/015* (2013.01); *A61B 1/04* (2013.01); *A61B 1/06* (2013.01); *A61B 1/307* (2013.01); *A61B 18/24* (2013.01); *A61B 34/25* (2016.02);

(Continued)

(58) Field of Classification Search
CPC ............ A61B 1/00048; A61B 1/00052; A61B 1/00045; A61B 1/00147
USPC .......................................................... 600/102
See application file for complete search history.

(56) References Cited

U.S. PATENT DOCUMENTS

| 5,928,137 A | * | 7/1999 | Green | ................ A61B 1/00052 600/104 |
|---|---|---|---|---|
| 2004/0243147 A1 | * | 12/2004 | Lipow | .................... A61B 34/35 606/130 |

(Continued)

OTHER PUBLICATIONS

International Search Report and Written Opinion for International Application No. PCT/US2017/015126, dated Apr. 12, 2017 (13 pages).

*Primary Examiner* — Alexandra L Newton
(74) *Attorney, Agent, or Firm* — Bookoff McAndrews, PLLC

(57) ABSTRACT

Exemplary aspects of a medical instrument system are disclosed. The system may have a support frame movably coupled to a patient table, the support frame having a computer display support, and an endoscope holder, wherein the computer display support and the endoscope holder are coupled to move together as a single unit. In some aspects, the system includes a computer display device, and an endoscope, wherein the computer display device and the endoscope are coupled to the support frame to move together as a single unit, and the patient table, computer display device, and the endoscope are arranged along a common longitudinal axis.

15 Claims, 3 Drawing Sheets

(51) Int. Cl.
*A61B 18/24* (2006.01)
*A61B 90/57* (2016.01)
*A61B 90/00* (2016.01)

(52) U.S. Cl.
CPC .............. *A61B 34/30* (2016.02); *A61B 34/74* (2016.02); *A61B 90/50* (2016.02); *A61B 90/37* (2016.02); *A61B 2034/301* (2016.02); *A61B 2090/571* (2016.02)

(56) References Cited

U.S. PATENT DOCUMENTS

| | | |
|---|---|---|
| 2005/0033117 A1 | 2/2005 | Ozaki et al. |
| 2005/0234293 A1* | 10/2005 | Yamamoto ......... A61B 1/00082 600/102 |
| 2007/0030344 A1 | 2/2007 | Miyamoto et al. |
| 2007/0299387 A1* | 12/2007 | Williams ........... A61B 1/00052 604/22 |
| 2008/0203280 A1* | 8/2008 | Rizoiu ................... A61B 18/18 250/227.11 |
| 2012/0004502 A1* | 1/2012 | Weitzner ............. A61B 1/0014 600/102 |
| 2012/0130159 A1 | 5/2012 | Abri et al. |
| 2014/0066701 A1 | 3/2014 | Wilson et al. |
| 2015/0150440 A1 | 6/2015 | Salvati et al. |
| 2015/0157188 A1 | 6/2015 | Moskowitz et al. |
| 2015/0265769 A1 | 9/2015 | Bratbak et al. |
| 2015/0297282 A1* | 10/2015 | Cadouri ............ A61B 18/1206 606/34 |
| 2017/0000320 A1 | 1/2017 | Wilson et al. |

\* cited by examiner

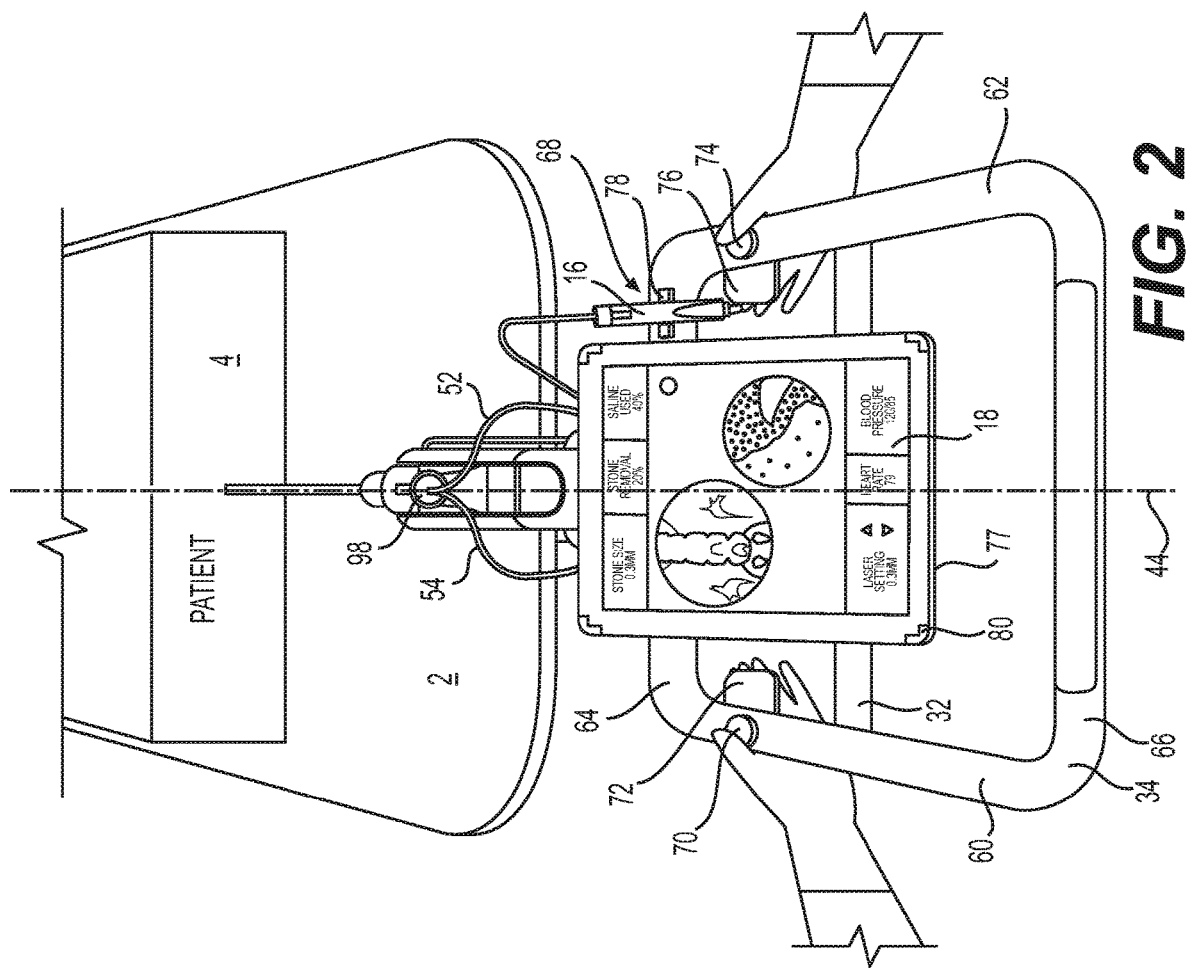

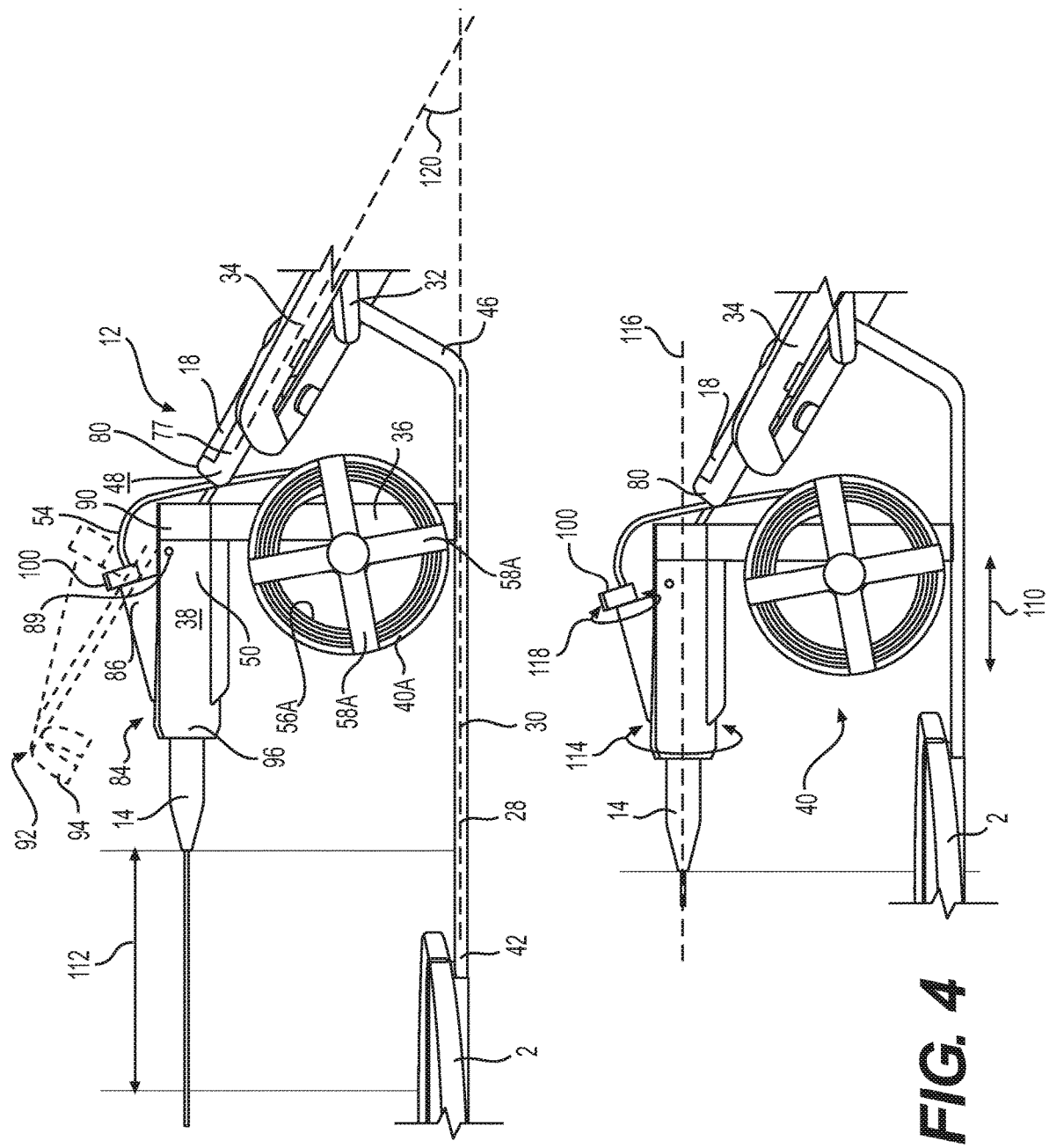

MEDICAL INSTRUMENT SYSTEM

CROSS-REFERENCE TO RELATED APPLICATIONS

This application claims the benefit of priority of U.S. Provisional Application No. 62/288,868, filed Jan. 29, 2016, the entirety of which is incorporated by reference into this application.

TECHNICAL FIELD

The present disclosure relates generally to medical instrument systems.

BACKGROUND

Retrieval devices and systems allow physicians and other medical professionals to remove various materials from a patient, including organic material (e.g., blood clots, tissue, and biological concretions such as urinary, biliary, and pancreatic stones) and inorganic material (e.g., components of a medical device or other foreign matter). For example, biological concretions can develop in the kidneys, pancreas, ureter, or gallbladder, and cause blockages or other complications within the body. Minimally-invasive medical procedures may be used to remove these materials through a natural orifice, such as lithotripsy and ureteroscopy, or through an incision, such as percutaneous nephrolithotomy.

Current ureteroscopic procedures typically require two or more people, wherein a physician controls the ureteroscope with both hands, using one hand to grasp the handle and the other to hold the distal portion of the ureteroscope as it enters the urinary tract via the urethral meatus. An assistant inserts, manipulates, and retracts a tool such as a stone retrieval basket, forceps, or a laser through a working channel of the ureteroscope. Thus, the procedure may require, among other things, controlling the movement of the ureteroscope into and out of the patient, steering the ureteroscope within the patient, movement of the tools through the ureteroscope, and actuation of the tools once they are positioned at a desired site.

With these various movements of the ureteroscope and tool is a desire by the physician to track such movement and monitor other aspects of the patient and the procedure. Currently, this information may be located at different locations within the operating room, requiring the physician to focus attention away from the holding and/or manipulating the ureteroscope and/or tools. The present disclosure is directed to these issues and other issues in the art.

SUMMARY

Aspects of the present disclosure relate to an endoscopic device and method. Numerous aspects of the present disclosure are now described.

One aspect is a medical system. This system may comprise a support frame movably coupled to a patient table, the support frame may have a computer display support, and an endoscope holder, wherein the computer display support and the endoscope holder are coupled to move together as a single unit.

Aspects of this system may additionally and/or alternatively include any one or more of the following features. The support frame and endoscope holder may share a common longitudinal axis. The computer display support may share a common longitudinal axis with the support frame and endoscope holder. The support frame may share a common longitudinal axis with the patient table. The support frame may further include at least one actuator for controlling an instrument coupled to the support frame. The instrument may be at least one of an endoscope, a stone retrieval basket, a laser unit, or a fluid generator. The support frame may be slidably coupled to the patient table. The computer display support may form a display plane at an acute angle with respect to a top plane of the patient table. The support frame may further include one or more spools. The support frame may further include a support beam, a vertical endoscope beam, and a handrail. The support beam may couple to the patient table, and the endoscope beam may be located distal of the handrail. The handrail may be positioned at approximately the same angle as a display plane of the computer display support. The system may further include at least one of an endoscope, a computer display device, a stone retrieval basket, a laser unit, or a fluid generator. The system may further include an instrument holder coupled to the handrail. The system may further include a ureteroscope received in the endoscope holder.

Another aspect is a medical instrument system. This system may comprise a support frame movably coupled to a patient table, the support frame having a computer display device, and a plurality of medical instruments, wherein the computer display device and the plurality of medical instruments are coupled to the support frame to move together as a single unit.

Aspects of this system may additionally and/or alternatively include any one or more of the following features. One of the plurality of medical instruments may include an endoscope. The computer display device may display one or more videos image from the endoscope, a medical procedure information, and a patient information. The computer display device and the endoscope may be coupled to the support frame to move together as a single unit. The patient table, the computer display device, and the endoscope may be arranged along a common longitudinal axis. The computer display device may be located proximal of the endoscope, while the endoscope may be located proximal of the patient table.

It may be understood that both the foregoing general description and the following detailed description are exemplary and explanatory only and are not restrictive of the invention, as claimed. As used herein, the terms "comprises," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 2 illustrates an end view of the medical instrument system of FIG. 1;

FIG. 3 illustrates a side view of the medical instrument system of FIG. 1 in a first position; and FIG. 4 illustrates a side view of the medical instrument system of FIG. 1 in a second position.

DETAILED DESCRIPTION

Figure 1:
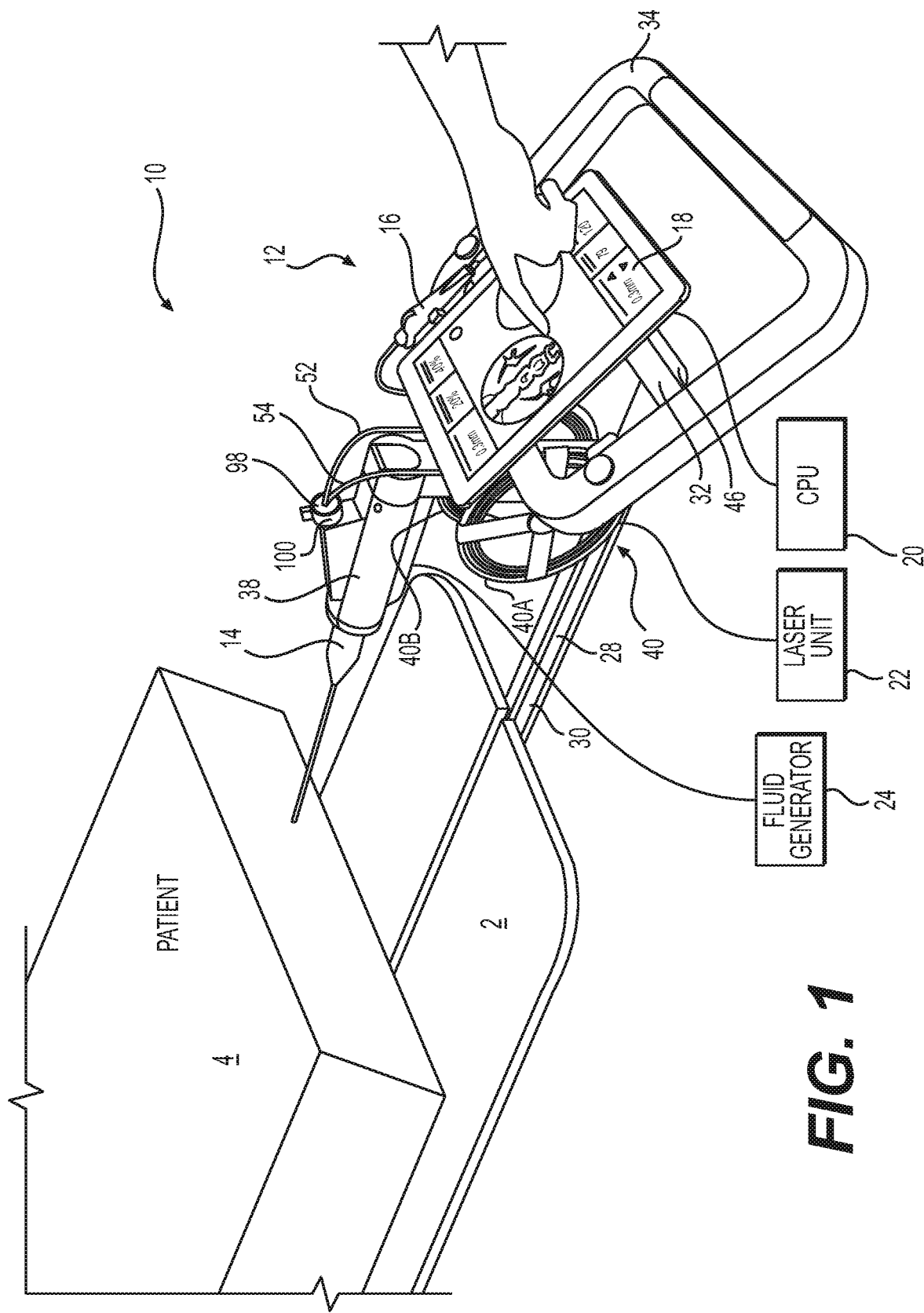
FIG. 1 illustrates a perspective view of the medical instrument system according to the present disclosure.

Reference is now made in detail to examples of the present disclosure, examples of which are illustrated in the accompanying drawings. Wherever possible, the same reference numbers will be used throughout the drawings to refer to the same or like parts. The terms "proximal" and "distal" are used herein to refer to the relative positions of the components of the instrument system. When used herein, "proximal" refers to a position relatively closer to a user of the instrument system. In contrast, "distal" refers to a position relatively farther away from the user of the instrument system. As used herein, the terms "generally," "approximately," and "substantially" indicate a range of +/−5% of the stated value.

FIG. 1 illustrates a perspective view of the medical instrument system 10 according to the present disclosure. The medical instrument system 10 is coupled to a patient table 2 that supports a patient 4 during a medical procedure. The medical instrument system 10 includes a support frame 12, an endoscope 14, a medical instrument 16, a computer display device 18, a central processing unit (or "CPU") 20 connected to the display device 18, a laser unit 22, and a fluid generator 24.

The laser unit 22 may be any type of laser unit, for example, a holmium laser unit, a holmium:YAG laser unit, a carbon dioxide laser unit, or another suitable laser unit. The fluid generator 24 may be any device and/or devices that can supply fluid (e.g., saline) to endoscope 14. The fluid generator 24 may include components such as a fluid source, a pump, a control system, a heat exchanger, a filter, a temperature sensor, a pressure sensor, a supply line, and/or various user input devices.

As best shown in FIGS. 1 and 3, the support frame 12 may include a primary support beam 30, a handrail support 32, a handrail 34, an endoscope support beam 36, an endoscope holder 38, and one or more spools 40. Any spool 40 may be used to hold a length of a fiber, or a length of a sheath, such as those forming part of a medical instrument sheath used in biopsy, lithotripsy. Exemplary uses of the one or more spools 40 are described further below. The primary support beam 30 may include a generally straight portion 28 having a distal end 42 slidably coupled to an underside of patient table 2. The primary support beam 30 may also include an angled proximal end 46 coupled to the handrail support 32. The coupling of the angled proximal end 46 of primary support beam 30 to the handrail support 32 may be a fixed connection as shown, or may be an adjustable connection via a rotatable and lockable joint or similar connection. Such an adjustable connection may allow the angle of the handrail support 32 and accompanying handrail 34 to be adjusted to a desired angle, such as angle 120 in FIG. 3.

As best seen in FIGS. 2 and 3, the handrail support 32 may include a beam extending normal to the primary support beam 30. The handrail 34 may be attached to both ends of the handrail support 32. Handrail support 32 may also be coupled to a computer display support 48 (FIG. 3) that will be described in more detail below. While handrail support 32 is shown as a straight beam in FIGS. 1-4, handrail support 32 could be formed in different configurations.

Referring again to FIG. 3, and as noted above, support frame 12 may include an endoscope support beam 36 extending vertically from support beam 30 to a height above a top of handrail 34. Endoscope support beam 36 may be rotatably connected to the endoscope holder 38 to allow for rotation of endoscope 14 and endoscope holder 38 about axis 116 (FIG. 4). This rotational connection between endoscope support beam 36 and endoscope holder 38 can be achieved by, for example, one or more tongue and groove connections (not shown) between a proximal end 50 of the endoscope holder 38 and a top portion 90 of support beam 36.

Endoscope support beam 36 (FIG. 3) may also be coupled to any of the one or more spools 40. As shown in FIG. 1, two spools 40 may be included, a first spool 40A for a laser fiber 54 associated with laser unit 22, and a second spool 40B for a sheath of medical instrument 16. First and second spools 40A and 40B may each be rotatably coupled about the endoscope support beam 36. The rotation of spools 40A, 40B may allow feeding and withdrawing of laser fiber 54 or sheath 52 of medical instrument 16 through a working channel of endoscope 14 during a medical procedure. Referring to FIG. 3, first spool 40A, for example, can be formed in any manner, and may include a base cylinder 56A on which the laser fiber 54 is spooled, and a plurality of sidewall members 58A on both sides of the based cylinder 56A to restrict movement of the laser fiber 54 axially on base cylinder 56A. Sidewall members 58A can also provide a gripping portion for manual control of spool 40A. Although not shown, second spool 40B of FIG. 1, like first spool 40A, may similarly include a base cylinder and sidewall member configured for use with sheath 52 of medical instrument 16. Either of the first and second spools 40A an 40B may be used independently with laser fiber 54 or sheath 52 of medical instrument 16.

Referring to FIG. 2, handrail 34 may include a pair of parallel side rails 60, 62, a top rail 64, and a bottom rail 66. The side, top and bottom rails 60, 62, 64, and 66 may form a generally square or rectangular shape, but it is understood that other shapes could be used. For example, handrail 34 may be of any shape that facilitates handling of the support frame 12 and supporting of display device 18, and need not necessarily include rails. The top rail 64 may include an instrument holder 68 for receiving a medical instrument. Side rails 60, 62, may include actuators 70, 72, 74, and 76 for controlling various aspects of the medical instrument system 10, as will be discussed in more detail below. Handrail 34 may also couple to display support 48 (FIG. 3) along top rail 64 to receive display device 18.

Instrument holder 68 (FIG. 2) may include at least one clip 78 extending from top rail 64 of handrail 34. The clip 78 may have a U or C shape and may be sized to receive a handle of medical instrument 16. The clip 78 may be flexible to provide a snap in fit for the medical instrument 16, or may be adjustable and lockable for receiving and securing medical instrument 16. The medical instrument 16 may be, for example, a stone retrieval basket, a grasper, or any other medical instrument appropriate for the desired medical procedure. The location of clip 78 on the top rail 64 positions the medical instrument 16 adjacent the endoscope 14 (or an associated one of the one or more spools 40) to facilitate, for example, a portion of the sheath 52 of the medical instrument 16 being fed over second spool 40B and through a working channel of the endoscope 14 to a desired patient site. Another clip 78 may be used with laser fiber 54.

Actuators 70, 72, 74, and 76 located on side rails 60, 62 may be in the form of buttons or levers, as shown, or may be any other type of actuator, such as switches, joysticks, and/or rollers. While the actuators 70, 72, 74, and 76 are shown on the side rails 60, 62, they may be located elsewhere, such as on top and/or bottom rails 64, 66. The actuators 70, 72, 74, and 76 may control various features of support frame 12, endoscope 14, medical instrument 16, laser unit 24, fluid generator 26, and/or any other feature or device of medical instrument system 10. For example, the actuators 70, 72, 74, and 76 may control fluid generator 26 to supply suction and/or irrigation fluid through the endoscope 14, control steering/deflection of a distal end of endoscope 14, control movement of the support frame 12 relative to patient table 2, control the rotation of the one or more spools 40, feeding or withdrawing of laser fiber 54 or sheath 52 directly, and/or actuation (opening/closing) of an end effector or basket of the medical instrument 16. Such control can be achieved through various motive systems and through a wired or wireless connection.

As noted above, the display support 48 (FIG. 3) may be coupled to top rail 64 of handrail 34 and to handrail support 32 so as to orient the display device 18 in a display plane that is parallel to a plane of the handrail 34. The display plane corresponds to the plane formed by the top/display surface of display device 18. Display plane of display device 18 may also form an acute angle with respect to a top plane of the patient table 2. Alternatively, display support 48 could be coupled to one or both of top rail 64 and handrail support 32 in a manner that would allow for adjustment of the display plane of the display device 18. Display support 48 may include a back plate or back frame 77 (FIGS. 2-3) that is sized to receive display device 18. For example, back frame 77 can be custom sized with flexible corner tabs 80 that fixedly grip corners of the display device 18. Alternatively, the back frame 77 can be adjustable to receive and secure display devices 18 of various sizes.

Computer display device 18 can be a tablet type computing system having a touch screen display and conventional computer components, such as a CPU, memory, video and graphics cards, wireless and wired networking devices, audio devices, one or more input/output ports, a power supply, and/or any other suitable computer features. The display device 18 may also form a computer with a separate CPU as shown in FIG. 1. While not shown in the figures, display device 18 may include connections to receive or send information from various patient monitoring systems and devices (e.g., an image) and/or other sensors of endoscope 14, laser unit 22, fluid generator 24, one or more spools 40, and/or any other component or feature of medical instrument system 10. Such connections may allow display device 18 to display patent information and vitals, video images from an image sensor of endoscope 14, procedure information such as a procedure timer, how much irrigation fluid (saline) has been used, and/or laser firing history and power. Display device 18 may also include actuators, physical or graphical, for controlling features of medical instrument system 10. For example, display device 18 may include actuators for controlling the withdrawal or feeding of the laser fiber 54 or sheath 52 of medical instrument 16 through the working channel of endoscope 14. Power may be supplied to display device 18 in any conventional manner, and the display device 18 can be controlled by activation of the touch screen, or by voice or gesture controls.

As noted above, endoscope 14 may be received in endoscope holder 38. Referring to FIG. 3, endoscope holder may include a top portion 84 including a port assembly 86 hingedly connected to a proximal end 50 of endoscope holder 38 by, for example, a hinge pin 89. In the open position (shown in dashed lines in FIG. 3), the port assembly 86 provides an opening in the top portion 84 of endoscope holder 38 to allow placement of the endoscope 14 therein. The port assembly 86 may include a distal end 92 forming a clip 94 for securing to a distal end of 96 of endoscope holder 38, or to the endoscope 14 itself, when the port assembly 86 is moved to a closed position to secure the endoscope 14. The opening and closing of port assembly 86 could be done manually as shown in FIG. 3, or selectively moved via a motor and one of actuators 70, 72, 74, or 76.

Port assembly 86 (FIG. 3) may also include a port 98 (FIG. 1) for receiving the laser fiber 54 and/or sheath 52 of medical instrument 16. The port assembly 86 may include an internal friction roller mechanism (not shown) that can grip the laser fiber 54 and/or sheath 52, and can be actuated automatically by one of actuators 70, 72, 74, 76 (FIG. 2) to feed or withdraw the laser fiber 54 and/or sheath 52. In addition or alternatively, port 98 may include a rotatable ring or toggle control 100 that enables rotation of the laser fiber 54 and/or sheath 52 as shown by double arrow 118 in FIG. 4. Rotatable ring 100 may be manually controlled to switch between the use of laser fiber 54 and/or sheath 52. For example, fiber 54 and/or sheath 52 may be manually passed through ring 100, or automatically passed through ring 100 using a feeder mechanism operable with actuators 70, 72, 74, 76.

According to one aspect, fiber 54 and sheath 52 are slip fit through a grommet in ring 100 that allows dynamic advancement/withdrawal through ring 100 using manual or motorized controls. The grommet may be a compressible element that is frictionally engageable with an exterior surface of either fiber 54 or sheath 52. For example, the grommet may allow advancement/withdrawal of fiber 54 and/or sheath 52 when in an uncompressed, low friction position; and rotation of either or both of fiber 54 or sheath 52 when in a compressed, high friction position. Grommet shape, length and material are such that rotation of ring 100 in either direction of double arrow 118 maintains enough friction for 45 degree rotation left or right. An exemplary grommet may be made of silicone robber. Ring 100 may also contain a cam feature such that rotation exerts radial compression of the grommet when ring 100 is rotated so as to create additional friction and further enable rotation of fiber 54 or sheath 52.

Endoscope 14 may be any conventional endoscope, such as a ureteroscope, or cystoscope, and may include for example, a light system, image sensor, and working channel (not shown). As noted above, the working channel may receive one or more of laser fiber 54, sheath 52 of medical device 16, irrigation fluid from fluid generator 26, and/or a guidewire (not shown). Communication and power connections (not shown) may extend from endoscope 14 to display device 18 and/or CPU 20 to supply the necessary information to display device 18.

During use of the medical instrument system 10, gross movement of the endoscope 14 with respect to the patient 4 can be achieved by manually or automatically moving the support frame 12 in the direction shown by arrows 110. This gross movement may be part of the endoscope insertion steps of the procedure and may include a movement of up to 300 mm as indicated by arrow 112 and a comparison of positions between FIG. 3 and FIG. 4. If moved manually, the support frame 12 can be pushed or pulled by handrail 34 with the hands or a chest/waist of the physician. Movement of the support frame 12 could also be achieved automatically, for example via a rack and pinion type drive system between the patient table 2 and the primary support beam 30, with actuation of the drive system via one of actuators 70, 72, 74, or 76 of handrail 34.

Fine motion of the laser fiber 54 and sheath 52 of medical instrument 16 through endoscope 14 may also be achieved manually or automatically. If manually, the physician can physically feed or withdrawal the laser fiber 54 and/or sheath 52 through endoscope 14. As noted above, port assembly 86 may optionally include an internal friction roller mechanism (not shown) that can grip the laser fiber 54 and/or sheath 52 and can be actuated via one of actuators 70, 72, 74, or 76 of handrail 34 to automatically feed or withdrawal the laser fiber 54 and/or sheath 52 within the working channel of endoscope 14.

Similarly, endoscope 14 may be rotated manually or automatically about axis 116 as shown by double arrow 114. This rotation, along with the steering/deflection of the distal end of endoscope 14 allows for approximately 360 degrees of movement of the distal end of endoscope 14.

Support frame 12 may be formed of any appropriate material, such as stainless steel. Further, while the present disclosure references the use of a ureteroscope type endoscope 14 and stone retrieval basket type medical instrument 16 in association with a ureteroscopy procedure, it is understood that the present medical instrument system 10 may be use with various other types of instruments and procedures.

Medical instrument system 10 provides a consolidated interface for controlling the motion of various components of the system, and for monitoring various aspects of the patient 4 and procedure. This is achieved, for example, by arranging the support frame 12, endoscope holder 36, endoscope 14, patient table 2, computer display support 48, and display device 18 generally about a common longitudinal axis 44 as shown in FIG. 2. Providing the display device 18 on the support frame 12 allows the physician to monitor instrument movement, procedure information, and patient information, all in the same direction of view with endoscope 14, medical instrument 16, and patient 4. Moreover, by providing the physician with hands free support of the instrumentation, system 10 may also reduce cognitive load and improve the ergonomics of procedures that otherwise require manual support of numerous devices. Further, the consolidation provided by medical instrument system 10 may allow the physician to sit during the medical procedure because many of the monitoring and control aspects of the procedure are reachable or viewable from the chair.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A medical instrument system, comprising:
a support frame movably coupled to a patient table, wherein the support frame shares a common longitudinal axis with the patient table and wherein the support frame is configured to slide relative to the patient table only along the common longitudinal axis, the support frame having:
  a computer display support, wherein the computer display support is configured to slide relative to the patient table only along the common longitudinal axis, and
  an endoscope holder, wherein the computer display support and the endoscope holder are coupled to move together as a single unit, wherein the endoscope holder includes an endoscope holder longitudinal axis, wherein an endoscope is configured to be coupled to the endoscope holder and rotate about the endoscope holder longitudinal axis.

2. The medical instrument system of claim 1, wherein the support frame includes a support beam connected to the computer display support and the endoscope holder longitudinal axis is offset from the support beam.

3. The medical instrument system of claim 2, wherein the computer display support shares the common longitudinal axis with the support frame and the patient table.

4. The medical instrument system of claim 1, wherein the support frame further includes at least one actuator for controlling an instrument coupled to the support frame, and wherein the instrument is at least one of the endoscope, a stone retrieval basket, a laser unit, or a fluid generator.

5. The medical instrument system of claim 1, wherein the support frame is slidably coupled to the patient table along the common longitudinal axis.

6. The medical instrument system of claim 1, wherein the computer display support forms a display plane at an acute angle with respect to a top plane of the patient table.

7. The medical instrument system of claim 1, wherein the support frame further includes at least one spool configured to receive a portion of at least one medical instrument, wherein the at least one spool includes an axis of rotation normal to the common longitudinal axis.

8. The medical instrument system of claim 1, wherein the support frame further includes a support beam, a vertical endoscope beam, and a handrail.

9. The medical instrument system of claim 8, wherein the support beam couples to the patient table, and the endoscope beam is located distal of the handrail.

10. The medical instrument system of claim 8, wherein the handrail is positioned at approximately the same angle as a display plane of the computer display support.

11. The medical instrument system of claim 8, further including at least one of an endoscope, a computer display device, a stone retrieval basket, a laser unit, a fluid generator, or an instrument holder coupled to the handrail.

12. The medical instrument system of claim 1, further including a ureteroscope received in the endoscope holder.

13. A medical instrument system, comprising:
a support frame movably coupled to a patient table, the support frame having:
  a computer display device,
  an endoscope, wherein the computer display device and the endoscope are coupled to the support frame to move together as a single unit, and the patient table, computer display device, and the endoscope are arranged along a common longitudinal axis; and
  a handle including a pair of side rails joined at a first end of each of the side rails by a top rail and joined at an opposite end of each of the side rails by a bottom rail, wherein the pair of side rails and the bottom rail are disposed outside a periphery of the computer display device, and wherein the handle is positioned at approximately the same angle as a display plane of the computer display device,
wherein the handle further comprises a central rail extending from a first side rail from the pair of side rails to the other side rail from the pair of side rails, wherein the central rail is disposed between the bottom rail and the top rail, and wherein the central rail couples the handle to the computer display device.

14. The medical instrument system of claim 13, wherein the computer display device is located proximal of the endoscope, and the endoscope is located proximal of the patient table.

15. The medical instrument system of claim 13, further comprising at least one actuator on the handle for controlling at least one aspect of the medical instrument system.

\* \* \* \* \*